(12) United States Patent
Cernosek et al.

(10) Patent No.: US 6,196,503 B1
(45) Date of Patent: *Mar. 6, 2001

(54) CABLE-TUBING ORGANIZER SYSTEM FOR MEDICAL CARE ENVIRONMENTS

(76) Inventors: Constance M. Cernosek, 1544 Prairie Grove Dr., Houston, TX (US) 77077; Richard M. Blenderman, 16207 La Terra, Houston, TX (US) 77083

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/895,969

(22) Filed: Jul. 17, 1997

(51) Int. Cl.[7] .............................. F16L 3/00; A47B 96/00; A47K 1/00; A47K 5/00
(52) U.S. Cl. .............................................. 248/51; 248/226
(58) Field of Search .................... 248/51, 74.1, 74.4, 248/70, 68.1, 231.51, 316.5, 687, 346.01, 346.03, 346.05; 24/495, 505, 518; 600/301, 102, 486, 485; 601/41

(56) References Cited

U.S. PATENT DOCUMENTS

| | | |
|---|---|---|
| 1,783,278 | 12/1930 | Brady . |
| 2,449,882 * | 9/1948 | Daniels ................................ 604/179 |
| 2,450,714 | 10/1948 | Campbell .............................. 248/51 |
| 2,459,711 | 1/1949 | Meier ................................... 248/226 |
| 2,510,198 | 6/1950 | Tesmer ................................. 248/226 |
| 2,525,398 * | 10/1950 | Collins ................................ 604/179 |
| 2,715,002 | 8/1955 | Davis ................................... 248/51 |
| 2,978,217 | 4/1961 | Gunderson ............................ 248/204 |
| 3,059,645 * | 10/1962 | Hasbrouck et al. .................. 604/179 |
| 3,194,235 * | 7/1965 | Cooke .................................. 128/888 |
| 3,231,845 | 1/1966 | Black et al. ........................... 339/29 |
| 3,242,311 | 3/1966 | Rutherford ........................... 219/130 |
| 3,312,434 | 4/1967 | Simon .................................. 248/62 |
| 3,510,151 * | 5/1970 | Weman ............................... 24/505 X |
| 3,529,797 | 9/1970 | Street .................................. 248/160 |
| 3,991,960 * | 11/1976 | Tanaka ................................ 248/68.1 |
| 4,023,757 | 5/1977 | Allard et al. ........................... 248/70 |
| 4,069,968 * | 1/1978 | Herman .............................. 233/14 R |
| 4,308,642 * | 1/1982 | Heyman .............................. 248/68.1 |
| 4,316,461 * | 2/1982 | Marais et al. ..................... 128/214 R |
| 4,323,212 | 4/1982 | Macaulay ............................. 248/51 |
| 4,342,218 * | 8/1982 | Fox .................................. 600/486 X |

(List continued on next page.)

FOREIGN PATENT DOCUMENTS

2258512    10/1993   (GB) .

*Primary Examiner*—Anita M. King
*Assistant Examiner*—Jerome DeLuca
(74) *Attorney, Agent, or Firm*—Akin, Gump, Strauss, Hauer & Feld L.L.P.

(57) ABSTRACT

A cable-tubing organizer system is provided for storing and organizing wire leads and tubing extending from monitoring equipment used in an operating room or other patient care environment. The organizer system includes a monitoring lead assembly, a transducer support device, and a transport plate. The monitoring lead assembly includes a plurality of clips, mounted on a base plate, for containing one or more coils of wire or tubing extending from operating room monitoring equipment. The monitoring lead assembly includes an attachment mechanism for securing the assembly to an operating table or any suitably convenient structure. The transducer support device includes a transducer bracket for securing a transducer holder that contains several different transducers. The transducer bracket translates vertically on a slotted plate for adjustment to patient chest level. The transducer support device includes a brace for containing wire leads or tubing and a base for insertion between an operating table and a mattress. The transport plate includes a transducer holder and a plurality of clips mounted on a breast plate for containing one or more coils of wire or tubing extending from a transducer.

10 Claims, 7 Drawing Sheets

U.S. PATENT DOCUMENTS

| | | | | |
|---|---|---|---|---|
| 4,453,933 | * | 6/1984 | Speaker | 604/179 |
| 4,546,774 | * | 10/1985 | Haught | 600/486 |
| 4,576,592 | * | 3/1986 | Danby | 604/80 |
| 4,582,281 | | 4/1986 | Van Camp | 248/51 |
| 4,625,936 | | 12/1986 | Hadden, Sr. | 248/544 |
| 4,669,484 | * | 6/1987 | Masters | 600/486 |
| 4,690,674 | | 9/1987 | Dalglish | 604/93 |
| 4,691,710 | * | 9/1987 | Dickens et al. | 600/486 |
| 4,702,231 | * | 10/1987 | Arpin | 601/41 |
| 4,705,243 | | 11/1987 | Hartmann et al. | 248/51 |
| 4,840,023 | | 6/1989 | Borsani | 59/78.1 |
| 4,889,303 | | 12/1989 | Wolf | 248/160 |
| 4,949,927 | | 8/1990 | Madocks et al. | 248/276 |
| 4,988,062 | * | 1/1991 | London | 248/68.1 |
| 5,102,399 | | 4/1992 | Chu | 604/250 |
| 5,106,366 | * | 4/1992 | Steppe | 604/30 |
| 5,135,189 | | 8/1992 | Ghazizadeh | 248/104 |
| 5,184,601 | | 2/1993 | Putman | 600/102 |
| 5,254,110 | * | 10/1993 | Marcus et al. | 248/68.1 X |
| 5,280,789 | * | 1/1994 | Potts | 600/486 |
| 5,361,756 | | 11/1994 | Cernosek | 600/301 |
| 5,716,035 | * | 2/1998 | Nourry et al. | 248/68.1 |
| 5,758,657 | * | 6/1998 | MacEachern | 600/485 X |
| 5,906,598 | * | 5/1999 | Gielser et al. | 604/251 |

* cited by examiner

CABLE-TUBING ORGANIZER SYSTEM FOR MEDICAL CARE ENVIRONMENTS

BACKGROUND OF THE INVENTION

1. Field of the Invention

The present invention relates generally to a system for the storage and organization of wire leads and tubes. In particular, the present invention relates to a system for the storage and organization of wire leads and tubes extending from monitoring equipment found in operating rooms, recovery rooms, and other patient treatment environments. Further, the present invention relates to a system for the storage and organization of wire leads and tubes during patient transport between various patient treatment environments.

2. Description of the Prior Art

Typically, a patient operating room or recovery room contains various invasive and non-invasive devices for monitoring patient vital signs and for patient treatment. For example, typical non-invasive patient monitoring equipment includes a pulse oxygen meter, an E.K.G., a blood pressure unit, and a temperature unit. In contrast, invasive monitoring equipment includes transducer units for determining systemic pressure, pulmonary artery pressure, and central venous pressure. For each monitoring unit, a lead of some type extends from the monitoring unit to the patient or the transducer units. These leads may be electrical cables or wires, as in the case of the pulse oxygen meter, the E.K.G., the temperature measurement unit and the transducer units. Alternatively, the leads may be tubing, such as the pneumatic tubing for the blood pressure monitoring units. In general, the length of the leads extending from the monitoring equipment is approximately four to twelve feet.

The extent of organization of the leads extending from the monitoring equipment varies greatly from operating room to operating room and from recovery area to recovery area. In general, however, no operating room nor recovery area protocol exists for storing the monitoring leads after their use. In fact, often the leads are discarded to the floor or left dangling from the monitors. As a result, the leads tend to knot up or become entangled with one another. This creates a cluttered work environment and causes stress to the operating room personnel because the leads must be located and untangled before they can be used again. Untangling the leads at the start of an operating room procedure or a recovery area hook-up takes valuable patient treatment time away from the nurses and doctors.

Leads lying on the floor also can cause the operating room work space to become unworkable because the leads can become entangled under foot or obstruct ready access to the patient. Additionally, such leads can become damaged by personnel stepping on them or rolling heavy equipment over them. Damaged leads require costly replacement because such leads are less effective at transmitting signals to the monitoring equipment.

Similarly, no protocol exists for organizing the transducer units and their associated wire leads during patient transport from the operating room to the recovery area or elsewhere. Typically, the wire leads that extend from the monitoring equipment to the transducers are disconnected from the monitoring equipment and haphazardly thrown on the patient gurney or patient. Little attention is given to keeping the wires from knotting or to keeping the wires separate from one another. Additionally, the transducers are randomly set on the gurney or patient. Thus, when the patient arrives in the recovery area, hospital personnel must untangle the wire leads extending from the transducers before reattaching them to the invasive monitoring equipment.

SUMMARY OF THE INVENTION

The present invention provides a system for organizing the various leads extending from operating room or recovery area monitoring equipment and leads extending from transducers transported with the patient during transition between the operating room and the recovery area. The cable-tubing organizer system of this invention is provided to store and organize the various leads extending from pulse oxygen metering units, E.K.G. units, temperature and blood pressure monitoring units, as well as the leads extending from the invasive monitoring equipment such as devices which measure systemic arterial pressure, pulmonary artery pressure, and central venous pressure. Additionally, the present invention is provided to store and organize leads extending from transducer units transported with the patient. Further, the present invention is provided to secure a transducer holder containing transducer units during an operating room procedure and during transport between the operating room and the recovery area.

The cable-tubing organizer system according to the present invention includes a monitoring lead assembly for temporarily storing the free ends of the wire or tubing leads of the monitoring equipment between operations or recovery area applications. The monitoring lead assembly includes a plurality of clips, mounted on a base plate, for containing one or more coils of wire or tubing extending from operating room or recovery area monitoring equipment. The monitoring lead assembly includes an attachment mechanism for securing the assembly to an operating table or other stationary object such as shelves which hold the monitoring equipment.

The cable-tubing organizer system further includes a transducer support device for securing a transducer holder and organizing the wire or tubing leads extending from the monitoring equipment during an operating room procedure. The transducer support device includes a transducer bracket for securing a transducer holder that contains several different transducers. The transducer bracket can translate vertically on a slotted plate for adjustment to patient chest level. One end of the slotted plate includes a brace for containing wire leads and pneumatic tubing. A second end of the slotted bracket includes a base for insertion between a mattress and an operating room table or gurney.

The cable-tubing organizer system according to the present invention further includes a transport plate for securing a transducer holder and for storing and organizing of wire leads that extend from transducers attached to the transducer holder. The transport plate includes a bracket for securing the transducer holder and a plurality of clips for containing the wire leads that extend from the transducers.

BRIEF DESCRIPTION OF THE DRAWINGS

A better understanding of the present invention may be had by reference to the following drawings and contained numerals therein of which.

DETAILED DESCRIPTION OF PREFERRED EMBODIMENT

Figure 1:
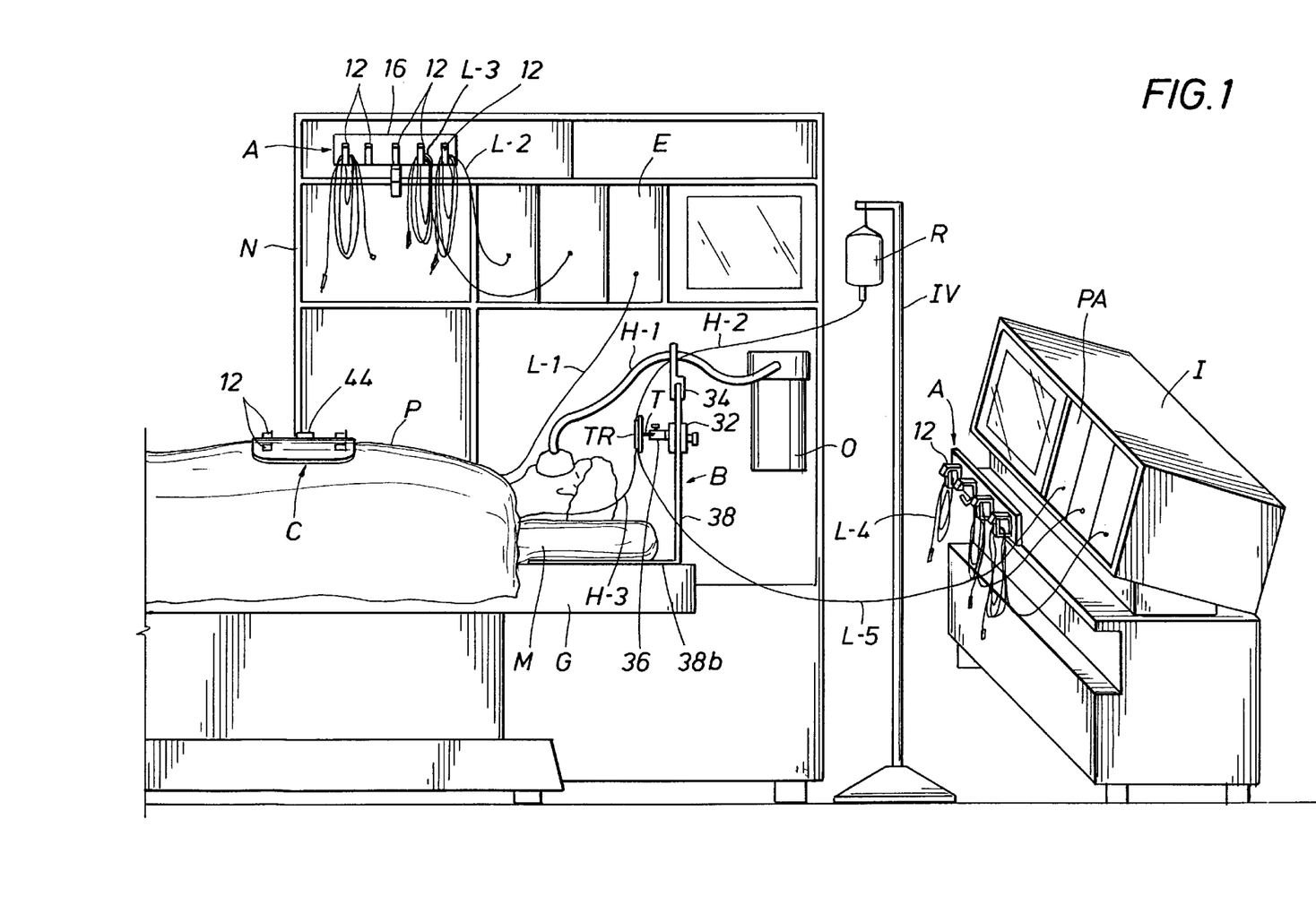
FIG. 1 is an isometric view of a typical operating room with the cable-tubing organizer system of the present invention.

Referring to the drawings and in particular to FIG. 1, a patient P is illustrated on a gurney G, which may be in an operating room, a clinic, or other location. Typically, during an operation an anesthesiologist (not shown) works near the head of the patient P near patient monitoring units. Although every operating room and recovery area is unique in its set-up of equipment, in general, to the right of the anesthesiologist is a bank of non-invasive monitoring equipment N that typically includes a pulse oxygen meter, an E.K.G., a blood pressure unit, and a temperature unit. Additionally, either behind or to the left of the anesthesiologist is an invasive monitoring equipment bank I that includes monitoring equipment for measuring systemic arterial pressure, pulmonary artery pressure, and central venous pressure. As shown, the lead L-1 from the E.K.G. unit E is just one of a number of leads that can extend from the bank of non-invasive monitoring equipment N to the patient during an operation. Similarly, lead L-5 from the pulmonary artery pressure unit PA is just one of several leads that can extend from the bank of invasive monitoring units I to a transducer holder T which holds several standard transducers for monitoring internal patient vital signs.

Without the devices of the present invention, the leads from the monitoring units and transducers fall on the operating room floor or dangle in a bundle before, during, and after an operation. Similarly, during patient transport from the operating room to the recovery area or during other patient movement, the leads rest on the patient P and become entangled with one another. The cable-tubing organizer system of the present invention is provided to contain these various leads extending from monitoring devices prior to and after their use. As shown in FIG. 1, and described in greater detail below, the cable-tubing organizer system of devices according to the present invention includes: a monitor lead assembly A for temporarily storing wire or tubing leads extending from invasive and non-invasive monitoring equipment; a transducer support device B for securing a transducer holder T and organizing the wire or tubing leads extending to and from transducers held by the transducer holder T; and a transport plate or breast plate C for securing the transducer holder T and storing leads extending from the transducers.

The devices of the cable-tubing organizer system allow doctors and nurses to organize the operating room quickly, efficiently, and easily prior to, during, and after surgery. Additionally, the devices allow easy organization of leads during patient transport from one treatment environment to another. In general, organization of equipment leads increases patient health and safety because it permits efficient access to the monitoring equipment and quicker attachment of the leads to the patient and monitoring equipment.

Figure 2:
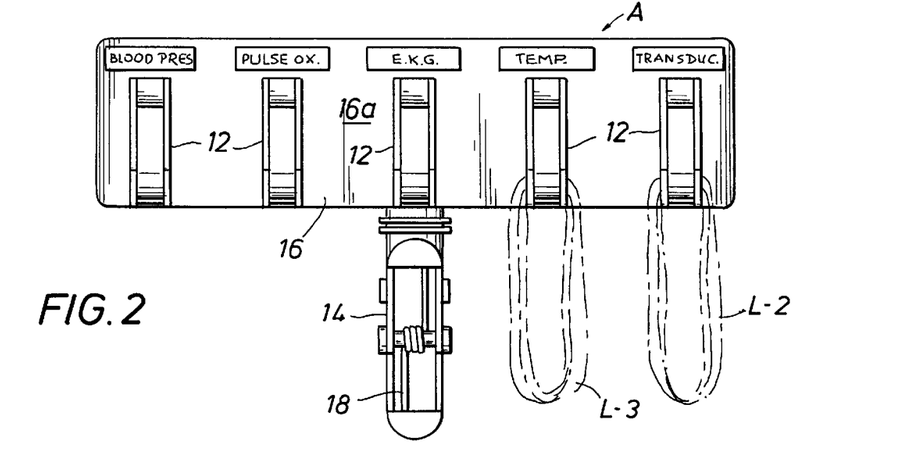
FIG. 2 is a front view of the monitor lead assembly of the present invention.

The monitoring lead assembly A of the present invention is further illustrated in the front view of FIG. 2. The monitoring lead assembly A is used to temporarily store leads L-2 and L-3 of monitoring equipment that are not in use during an operating room procedure. As shown in FIG. 1, leads such as L-1 and L-5 extend from the monitoring equipment to the patient P or to the transducer during an operation. At the end of the operation, these leads, which can range in length to six feet or more, must be stored until the next operation or procedure. The monitoring lead assembly A provides easy temporary storage of such leads.

Figure 3:
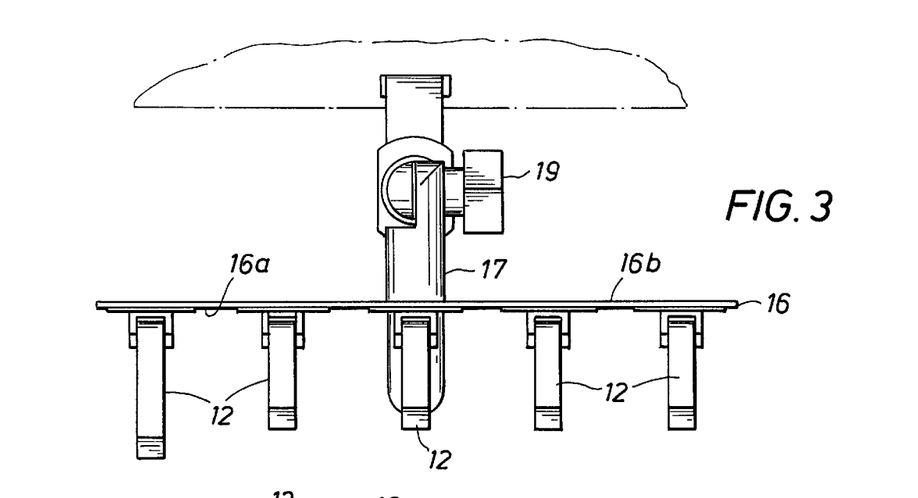
FIG. 3 is a plan view of the monitor lead assembly of FIG. 2.
Figure 4:
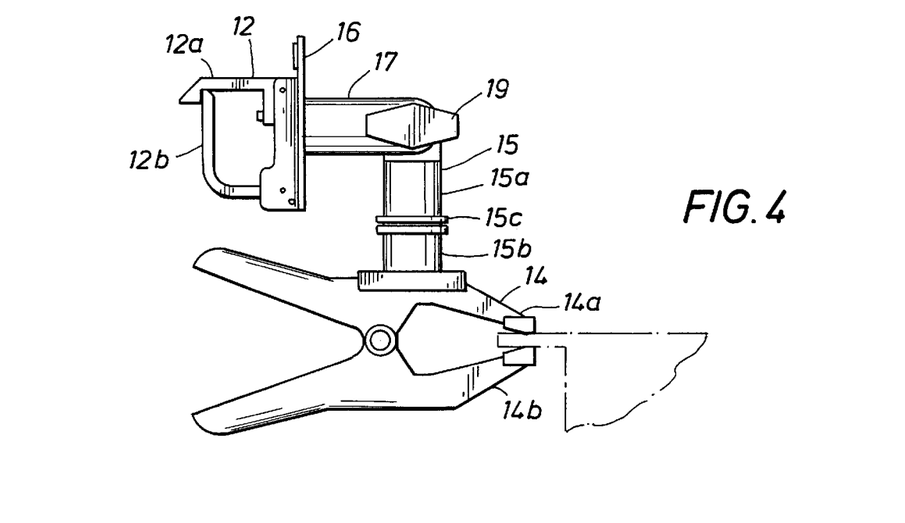
FIG. 4 is a side view of the monitor lead assembly of FIG. 2.

Referring to FIGS. 2–4, the monitoring lead assembly A includes a rectangular base plate 16 having a plurality of generally rectangular clips 12 mounted onto a front surface 16a of the base plate 16. The clips 12 provide an easily accessed storage means for coiled leads such as L-2 and L-3 that generally extend from monitoring equipment. The monitoring lead assembly A also includes a post 17 attached to a rear side 16b of the base plate 16 for mounting the monitoring lead assembly A to a table, shelf, or any other appropriate fixture found in an operating room or recovery area. In the preferred embodiment, the post 17 is pivotally attached to an upper portion 15a of a rotatable stud 15 by a bolt (not shown) with an attached knob 19. The knob 19 allows for easy adjustment of the position of the post 17.

The stud 15 includes the upper portion 15a threadably connected to a lower portion 15b. The threaded connection permits the upper portion 15a to frictionally rotate 360°, with respect to the lower portion 15b, about an axis extending longitudinally through both portions 15a and 15b. A gasket 15c seals any gap between the upper portion 15a and the lower portion 15b. The lower portion 15b of the stud 15 secures to a hand-operated spring clamp 14 for easy mounting of the monitoring lead assembly A to any suitable fixture. The spring-biased clamp 14 is of a well-known commercial variety and includes two clamping members 14a and 14b interconnected for pivotal movement and spring-biased to a closed position by a spring 18. The spring-biased clamp member 14 may be coated with a plastic sheath so that the clamp may be easily cleaned as necessary. Alternatively, the stud 15 of the monitoring lead assembly A can be permanently affixed to any suitable fixture by means of a nut and bolt combination (not shown) or the base plate 16 can be bolted directly to a fixture (not shown). Also, the spring-biased clamp member 14 can be secured directly to the base plate 16, by means of screws or a nut and bolt combination, for temporarily mounting the monitoring lead assembly A to a fixture.

Figure 5:
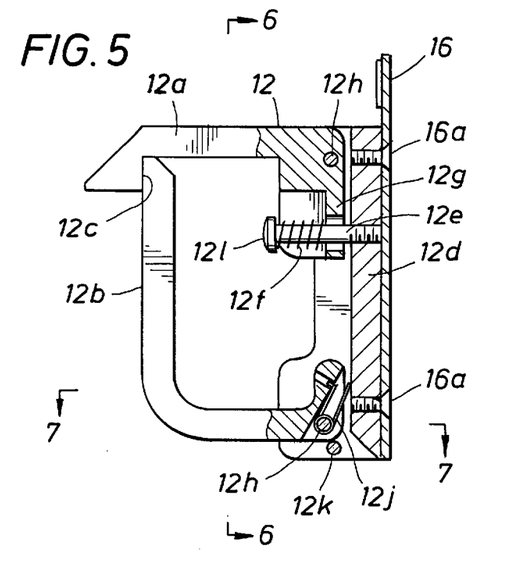
FIG. 5 is a side view, partially in section, illustrating one of the clips of the monitor lead assembly of FIG. 2.
Figure 8:
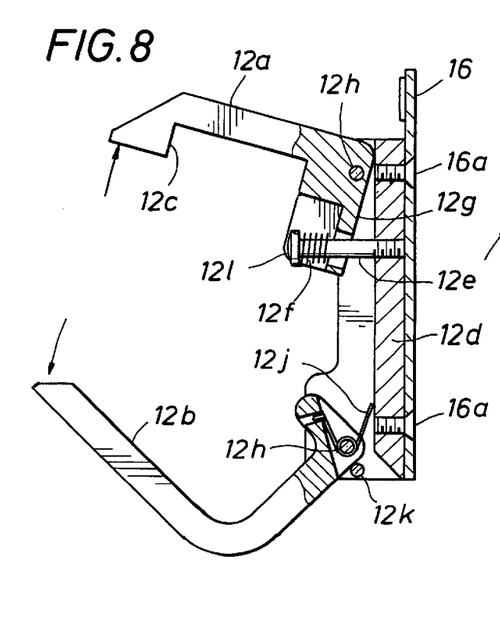
FIG. 8 is a side view, partially in section, illustrating operation of one of the clips of the monitor lead assembly of FIG. 2.
Figure 9:
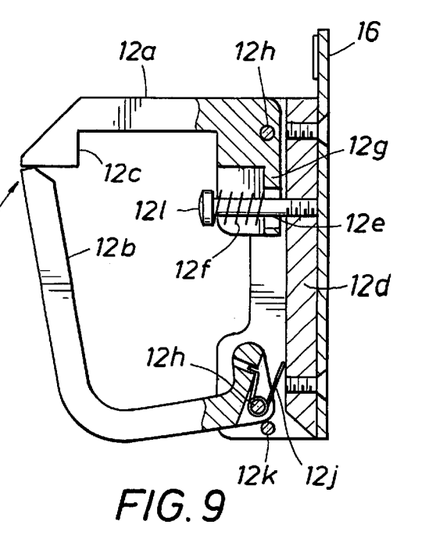
FIG. 9 is a side view, partially in section, illustrating operation of one of the clips of the monitor lead assembly of FIG. 2.

Referring to FIG. 5, the clip 12 is shown in its closed position. In general, the clip 12 includes a base 12d which can be attached to the base plate 16 by bolts such as 16a. Additionally, the clip 12 includes a lever 12a and an L-shaped hook 12b each pivotally attached to opposite ends of the base 12d. The hook 12b is L-shaped such that one end contacts a notch 12c of the lever 12a when the clip 12 is in the closed position. As shown in FIG. 8, the clip 12 is opened by pushing up on the lever 12a, which disengages the hook 12b from the notch 12c, thus permitting the hook 12b to pivot into its opened position. Once the hook 12b is in its opened position, coiled wire or tubing leads can be easily placed on or removed from the hook 12b. As shown in FIG. 9, the clip 12 can be closed simply by pivoting the lever 12a and the hook 12b such that they contact one another on the notch 12c of the lever 12a. As shown in FIG. 5, the lever 12a and the hook 12b cooperate to provide a generally rectangular space to receive coils of wire or tubing. Preferably, the monitor lead assembly A, including the individual clips 12, are made of aluminum or similar strength material.

Referring to FIGS. 5–9, to facilitate the opening and closing of the clip 12, both the lever 12a and hook 12b are spring-biased into contact with one another. The hook 12b is biased toward its open position (FIG. 8), whereas the lever 12a is biased toward its closed position (FIG. 5). This biasing assists the hook 12b in pivoting to its open position (FIG. 9) when the hook 12b is not in contact with the notch 12c. Moreover, the biasing of the hook 12b keeps the clip 12 tightly closed when the hook 12b is in contact with the notch 12c. Similarly, the biasing of the lever 12a toward its closed position keeps the clip 12 tightly closed and allows the hook 12b to snap into the closed position.

Figure 6:
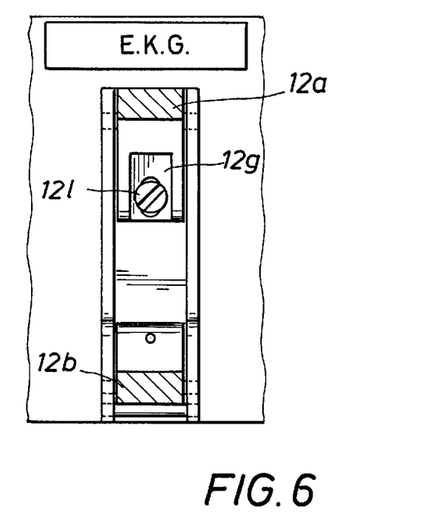
FIG. 6 is a view, partially in section, taken along line 6—6 of FIG. 5.
Figure 7:
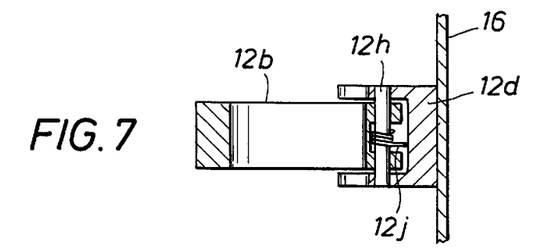
FIG. 7 is a view, partially in section, taken along line 7—7 of FIG. 5.

As shown in FIGS. 5, 8, and 9, a spring 12f is used to bias the lever 12a toward its closed position. Referring to FIGS. 5 and 6, the spring 12f is mounted on a bolt 12e and contacts a pivot arm 12m of the lever 12a. As shown in FIGS. 8 and 9, the compressed spring 12f pushes on the pivot arm 12g such that when the lever 12a is pivoted about a pin 12h to the open position, the lever 12a springs back into the closed position without any human intervention. In contrast, as shown in FIGS. 5, 7, 8, and 9, a spring 12j mounted between the hook 12b and the base 12d pushes on the hook 12b such that when the hook 12b is not constrained by the notch 12c, the hook 12b pivots about the pivot pin 12h to its open position. A stop 12k limits the angle through which the hook 12b can pivot. Although springs are used to bias the lever 12a and the hook 12b, any suitable biasing means can be employed.

Figure 11:
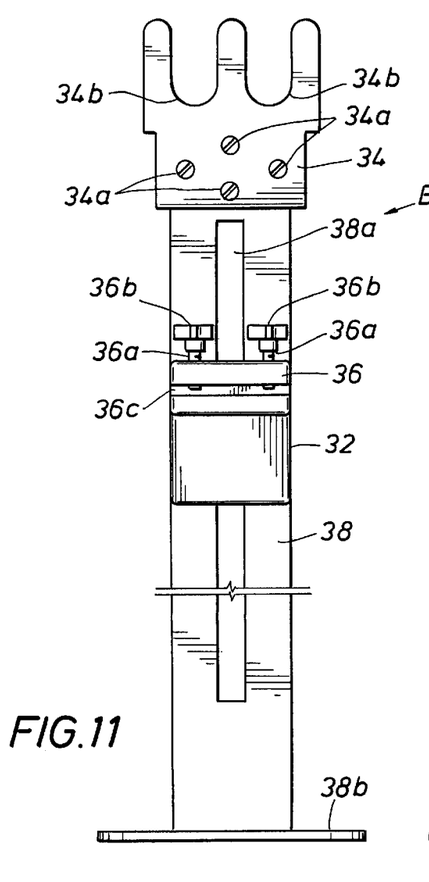
FIG. 11 is a front view of the transducer support assembly of the present invention.
Figure 12:
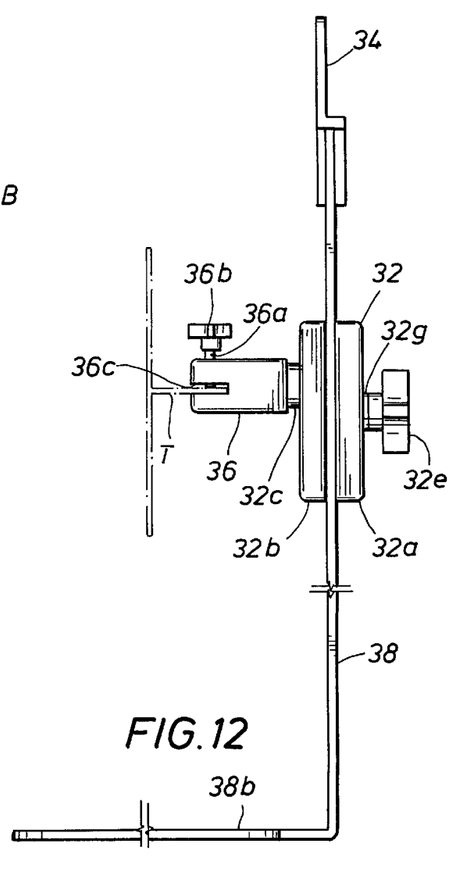
FIG. 12 is a side view of the transducer support assembly of FIG. 11.

The transducer support device B of the present invention is illustrated in FIGS. 1, 11, and 12. During an operation, a transducer bracket 36 of the transducer support device B secures a transducer holder T which contains several different transducers TR. The transducers TR measure various patient pressures, such as systemic arterial pressure, pulmonary artery pressure, and central venous pressure. As shown in FIG. 1, the transducer TR measures arterial pressuresthrough the use of a reservoir R and two saline hoses H-2 and H-3 and transmits the pressure electronically to the monitoring equipment through wire lead L-5. In operation, the reservoir R supplies a flushing pressure of saline solution through the hoses H-2 and H-3 to an artery or vein within the patient's P body cavity. The flushing pressure prevents blood clotting at the junction of blood vessel and an inserted catheter which is at a patient end of the saline hose H-3. The saline is not discharged into the artery or vein but, rather, moves within hose H-3 when the pressure in the artery or vein changes. The transducer TR monitors the pressure changes within hose H-3 and translates the results into electrical signals which are sent to the monitoring equipment through wire lead L-5.

Significantly, the transducers TR measure most accurately when located at the patient's chest level. Thus, the transducer bracket 36 is fully adjustable to the chest height of a small child or to that of a large adult. Additionally, as shown in FIG. 1, the transducer support device B includes a brace 34 for containing breathing hoses H-1 extending from oxygen tank 0, transducer hoses H-2, or invasive monitoring leads.

Figure 13:
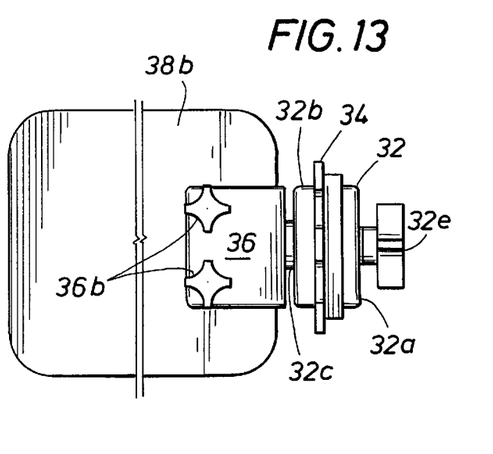
FIG. 13 is a plan view of the transducer support assembly of FIG. 11.

Referring to FIGS. 11–13, the transducer support device B includes the transducer bracket 36 rotatably mounted to a carriage 32. The carriage 32 translates vertically on a slotted plate 38 so that the transducer bracket 36, and thus the transducers TR, can be positioned at the patient's chest level for accurate recording of transducer measurements. The positioning of the transducers TR at chest level also provides an convenient location for extracting a blood sample. Additionally, as shown in FIG. 16, the transducer bracket 36 can be rotated about an axis transverse to the carriage 32 to fine tune the position of the transducers.

Figure 16:
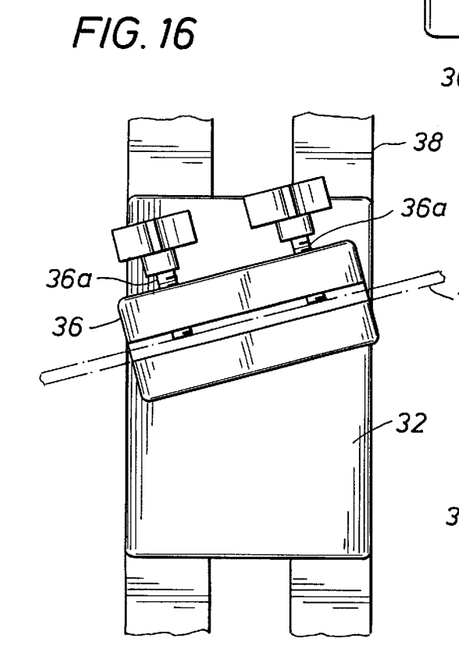
FIG. 16 is an enlarged front elevational view of FIG. 11.

Referring to FIGS. 11, 12, and 16, the transducer holder T fits into a transducer slot 36c on the transducer bracket 36. Bolts 36a secure the transducer holder T in place. As shown in FIGS. 11–13, the preferred embodiment includes bolts 36a with attached knobs 36b for easy fastening of the transducer holder T within the transducer slot 36c. The transducer bracket 36 is preferably made of aluminum or similar strength material.

Figure 14:
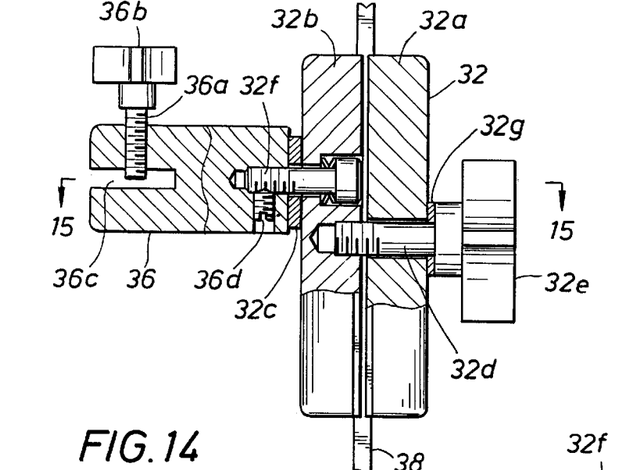
FIG. 14 is a side view, partially in section, of FIG. 11.
Figure 15:
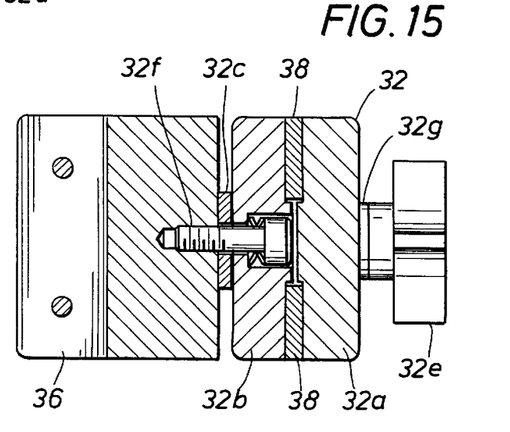
FIG. 15 is a view, partially in section, taken along line 15—15 of FIG. 14.

Referring to FIGS. 14 and 15, the preferred embodiment of the carriage 32 includes a back guide 32a and a front guide 32b each mounted on opposite faces of the slotted plate 38 and secured together by a bolt 32d inserted through the back guide 32a and the slot 38a and threaded into the front guide 32b. A knob 32e attached to the bolt 32d allows for easy adjustment of the carriage 32. Similarly, the transducer bracket 36 is rotatably mounted to the carriage 32 by a bolt 32f inserted through the front guide 32b and a rubber washer 32c and threaded into the transducer bracket 36. A set screw 36d prevents the bolt 32f from backing out after only a few rotations of the transducer bracket 36.

Figures 18, 19:
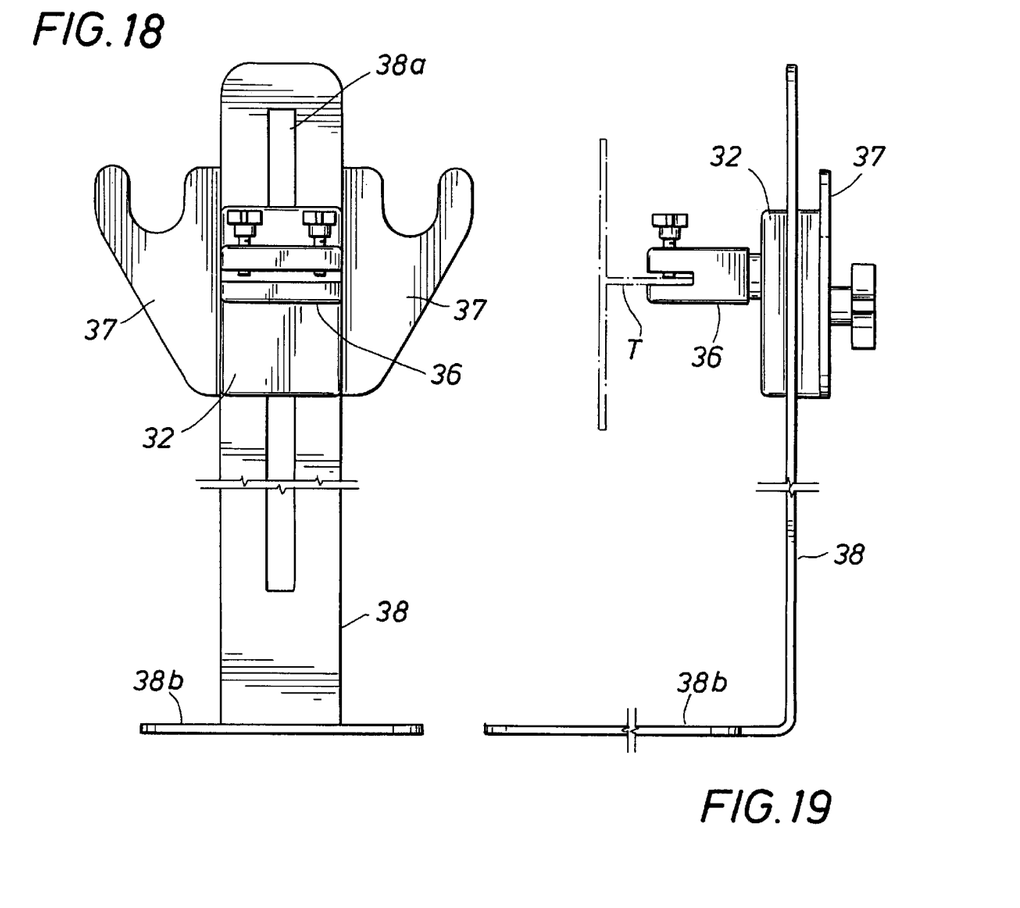
FIG. 18 is a front view of an alternative embodiment of the transducer support assembly of the present invention.
FIG. 19 is a side view of an alternative embodiment of the transducer support assembly of FIG. 18.
Figure 20:
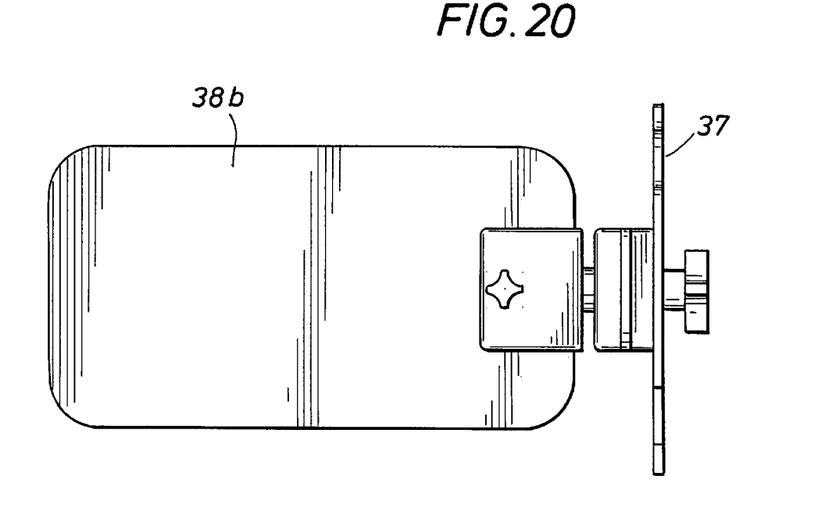
FIG. 20 is a plan view of the transducer support assembly of FIG. 18.

As shown in FIGS. 11 and 12, the slotted plate 38 includes the brace 34 for supporting and containing breathing hoses H-1, transducer hoses H-2, or invasive monitoring leads. The brace 34 is attached by nuts and bolts or screws such as 34a to one end of the slotted bracket 38. Additionally, the brace 34 includes slots 34b for supporting and containing the hoses or wire leads. Alternatively, as shown in FIGS. 18, 19, and 20, a brace 37 can be attached to the carriage 32. In this embodiment, if the transducers are not in use, the support bracket 37 can be moved to any convenient height for supporting and containing the hoses or wire leads.

Although the slotted plate 38 can be attached directly to the operating table through nuts and bolts, it is preferable to have a base support 38b so the transducer support device B is free standing. As shown in FIG. 1, the base support 38b fits between the mattress M and the operating room table or gurney G. The base support 38b allows the transducer support device B to be moved into any convenient position for aligning the transducers or supporting the hoses or wire leads.

Figure 10:
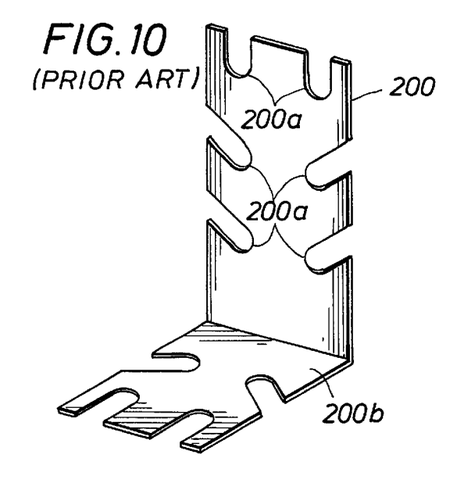
FIG. 10 is an isometric view of a prior art device for supporting breathing hoses.
Figure 17:
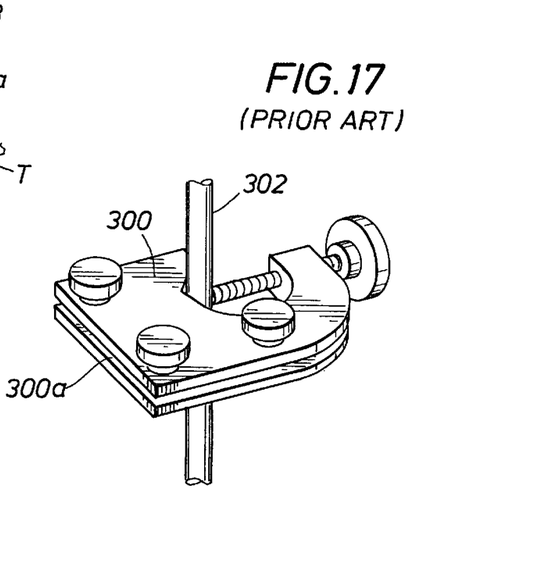
FIG. 17 is an isometric view of a prior art embodiment of a transducer support bracket.

The transducer support device B combines and improves upon features of the two unrelated prior art devices shown in FIGS. 10 and 17. A prior art "Christmas tree" 200 is shown in FIG. 10. The Christmas tree 200 is used in the operating room to support breathing tubes or any other hose or wire lead. It has several support slots 200a for receiving hoses and leads. Because of its base 200b, the Christmas tree 200 is free standing. The Christmas tree 200, however, cannot secure or position a transducer holder for use during an operation. In contrast, as shown in FIG. 17, the prior art transducer bracket 300 can secure a transducer holder in slot 300a but it cannot support and contain hoses and wire leads. Moreover, the transducer bracket 300 is not free standing but rather must be mounted on an I.V. pole IV (FIG. 1) or a rod 302 which is attached to the operating table. Also, although the transducer bracket 300 can translate up and down the rod 302, it cannot rotate about an axis transverse to the rod 302.

The transport plate or breast plate C of the present invention is illustrated in FIGS. 1 and 21–23. The breast plate C is used to secure the transducer holder T and temporarily store the tubing or wire leads extending from the patient or the transducers during patient transport from the operating room to the recovery area or elsewhere. Once the patient arrives in the recovery area, the transducer holder T is secured into the recovery area transducer support device B and the tubing or wire leads are plugged into the non-invasive and invasive monitoring equipment.

Figure 21:
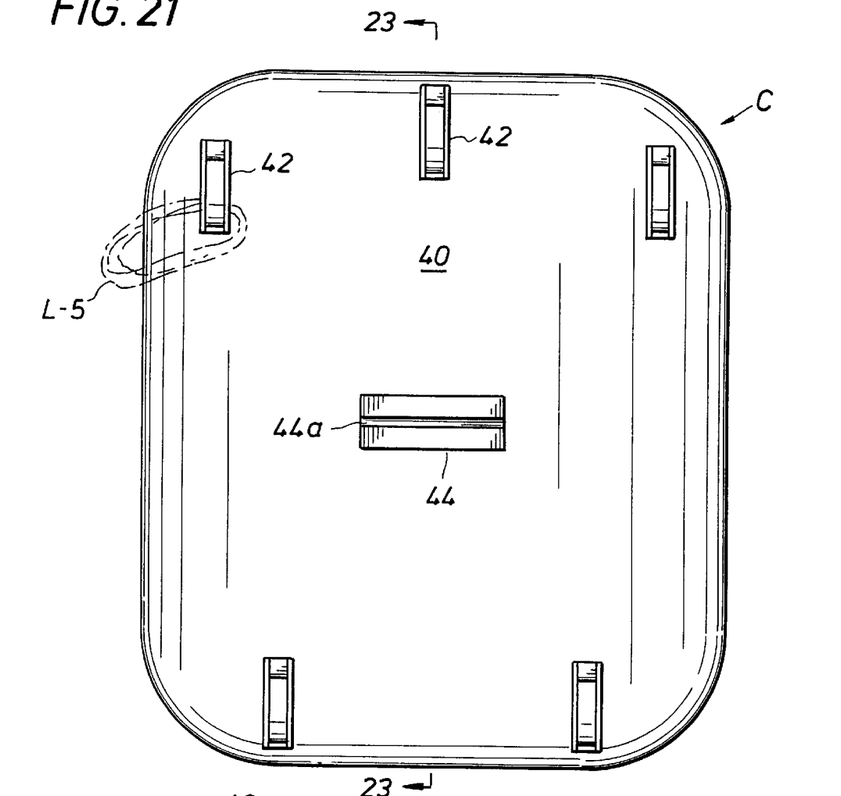
FIG. 21 is a plan view of the transport plate of the present invention.
Figure 22:
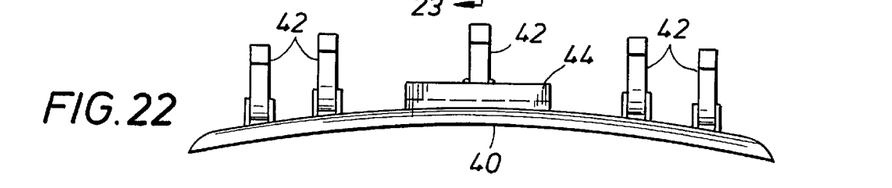
FIG. 22 is a side view of the transport plate of FIG. 21.
Figure 23:
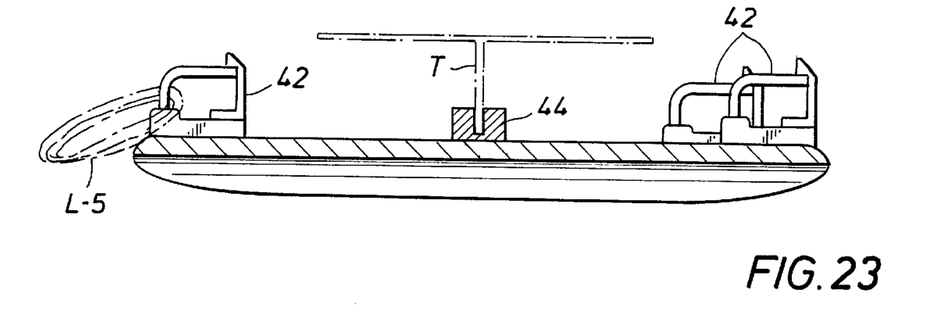
FIG. 23 is a view, partially in section, taken along line 23—23 of FIG. 21.

The generally arcuate breast plate C includes a plurality of clips 42 mounted on the top side of plate 40 which is rectangular as viewed from the top, as shown in FIG. 21, and curved as viewed from the side, as shown in FIG. 22. Each of the clips 42 is identical to the clips 12 and thus need not be further described. With the clips 42 in the open position such as illustrated for clip 12 in FIG. 8, the free ends of the wire leads extending from the transducers can be coiled onto the open interior of the clips 42. The clips 42 are then closed such that the clips 42 hold several rounds of coils of the free ends of the leads. The clips 42 are attached to the plate 40 by suitable screws or bolts. Preferably, the breast plate C and clips 42 are made of aluminum or other suitable material.

The breast plate C also includes a transducer bracket 44 mounted on the top side of the plate 40. The transducer bracket 44 secures the transducer holder T during patient transport. Although the transducer bracket 36 described above can be used on the breast plate C, the transducer bracket 44 is slightly different. In general, the transducer bracket 44 is constructed of hard rubber and the transducer holder T fits snugly into transducer slot 44a. Preferably, no bolts are used to secure the transducer holder T into transducer slot 44a. The transducer bracket 44 is attached to the plate 40 by suitable screws or bolts.

The foregoing disclosure and description of the invention is illustrative and explanatory thereof, and various changes in the size, shape, and materials as well as in the details of illustrative construction and assembly, may be made without departing from the spirit of the invention.

What is claimed is:

1. A transport plate device for storing and organizing wire leads and tubing extending from a transducer during patient transit from a first location to a second location comprising:

a breast plate having an edge perimeter, a top side, and a bottom side which is adapted for positioning the transport plate device on the person of the patient;

a transducer bracket having a slot for snugly securing a transducer holder, said transducer bracket mounted to said top side of said breast plate and positioned interiorly from said edge perimeter of said breast plate;

a plurality of clips for receiving and storing coiled wire, each of said clips mounted to said top side of said breast plate, wherein each of said clips includes:

a base having a first end and a second end;

a hook for receiving and storing the coiled wire, said hook having a first end and a second end, said first end pivotally attached to said first end of said base;

a lever having a first end pivotally mounted to said second end of said base and a second end extending transversely from said base and having a notch therein for receiving said second end of said hook;

a first biasing means for biasing said lever into a closed position; and a second biasing means for biasing said hook into an open position.

2. A transport plate device for storing and organizing wire leads and tubing extending from a transducer during patient transit from a first location to a second location comprising:

a breast plate having an edge perimeter, a top aide, and a generally smooth arcuate bottom side which is adapted for positioning the transport plate device on the torso of the patient;

a transducer bracket having a slot for snugly securing a transducer holder, said transducer bracket mounted to said top side of said breast plate and positioned interiorly from said edge perimeter of said breast plate;

a plurality of closeable clips having a hook member adapted for receiving and storing coiled wire, each of said clips mounted to said top side of said breast plate.

3. The transport plate device according to claim 2, wherein said bottom side of said breast plate includes a generally unobstructed surface.

4. A method for transporting a patient and a transducer with wire leads and tubes, the method comprising the steps of:

placing a breast plate on the patient;

securing the transducer to a transducer bracket of the breast plate;

coiling and storing the wire leads and tubes of the transducer in clips of the breast plate; and moving the patient from a first location to a second location.

5. The method for transporting a patient and transducer according to claim 4, further comprising the steps of:

removing the transducer from the breast plate at the second location;

plugging the transducer wire leads and tubes into monitoring equipment; and removing the breast plate from the patient.

6. The method for transporting a patient and transducer according to claim 4, wherein said step of securing the transducer to a transducer bracket is accomplished by sliding a transducer holder of the transducer into a slot on the transducer bracket.

7. The method for transporting a patient and transducer according to claim 4, wherein said step of moving the patient is accomplished by pushing the supine patient on a movable gurney.

8. A method for containing transducer wire leads and tubes after a patient procedure, the method comprising the steps of:

placing a breast plate on the torso of the patient;

securing the transducer to a transducer bracket of the breast plate; and storing the transducer wire leads and tubes in clips of the breast plate.

9. The method for containing transducer wire leads and tubes according to claim 8, wherein said step of securing the transducer to a transducer bracket is accomplished by sliding a transducer holder of the transducer into a slot on the transducer bracket.

10. The method for containing transducer wire leads and tubes according to claim 8, wherein said step of storing the transducer wire leads and tubes is accomplished by coiling the wire leads and tubes and placing them over a hook member of the clips.

* * * * *